United States Patent [19]
Cooper et al.

[11] Patent Number: 5,326,923
[45] Date of Patent: Jul. 5, 1994

[54] METHOD FOR REGENERATING CERTAIN ACIDIC HYDROCARBON CONVERSION CATALYSTS BY SOLVENT EXTRACTION

[75] Inventors: Michael D. Cooper; Pradip Rao, both of San Jose; David L. King, Mountain View; Ronald R. Lopez, San Jose, all of Calif.

[73] Assignee: Catalytica, Inc., Mountain View, Calif.

[21] Appl. No.: 796,940

[22] Filed: Nov. 22, 1991

Related U.S. Application Data

[63] Continuation-in-part of Ser. No. 588,448, Sep. 26, 1990, abandoned, Ser. No. 697,318, May 7, 1991, Pat. No. 5,157,197, and Ser. No. 697,320, May 7, 1991, abandoned.

[51] Int. Cl.$^5$ .......................... C07C 2/58; B01J 20/34
[52] U.S. Cl. .................................. 585/725; 585/709; 585/721; 585/722; 585/724; 585/726; 585/727; 585/728; 502/22; 502/29; 502/33
[58] Field of Search ............... 585/709, 721, 722, 725, 585/726, 727, 728, 724; 502/22, 29, 33

[56] References Cited

U.S. PATENT DOCUMENTS

| | | | |
|---|---|---|---|
| 2,284,156 | 2/1958 | Kelly et al. ...................... | 585/465 |
| 2,405,565 | 8/1946 | Fawcett et al. . | |
| 2,406,869 | 9/1946 | Upham . | |
| 2,748,090 | 5/1956 | Watkins ........................... | 502/203 |
| 2,804,491 | 8/1957 | May et al. ....................... | 585/726 |
| 2,824,146 | 2/1958 | Kelly et al. ...................... | 585/465 |
| 2,824,150 | 2/1958 | Knight et al. .................... | 585/465 |
| 2,824,151 | 2/1958 | Kelly et al. ...................... | 585/465 |
| 2,824,152 | 2/1988 | Knight et al. .................... | 585/465 |
| 2,824,153 | 2/1958 | Kelly et al. ...................... | 585/465 |
| 2,824,154 | 2/1958 | Knight et al. .................... | 585/465 |
| 2,824,155 | 2/1958 | Knight et al. .................... | 585/726 |
| 2,824,156 | 2/1958 | Kelly et al. ...................... | 585/465 |
| 2,824,157 | 2/1958 | Knight et al. .................... | 585/465 |
| 2,824,158 | 2/1958 | Kelly et al. ...................... | 585/465 |
| 2,824,159 | 2/1958 | Kelly et al. ...................... | 585/465 |
| 2,824,160 | 2/1958 | Knight et al. .................... | 585/465 |
| 2,824,161 | 2/1958 | Knight et al. .................... | 585/465 |
| 2,824,162 | 2/1958 | Knight et al. .................... | 585/465 |
| 2,939,890 | 6/1960 | Hervert et al. . | |
| 2,945,907 | 7/1960 | Knight et al. .................... | 585/726 |
| 2,971,037 | 2/1961 | Gilbert et al. .................... | 585/727 |
| 2,972,649 | 2/1961 | Thomas et al. ................... | 585/729 |
| 2,976,338 | 3/1961 | Thomas ............................ | 585/525 |

(List continued on next page.)

FOREIGN PATENT DOCUMENTS

| | | |
|---|---|---|
| 1346135 | 1/1963 | France . |
| 2504121 | 10/1982 | France . |
| WO90/00533 | 1/1990 | PCT Int'l Appl. . |
| WO90/00534 | 1/1990 | PCT Int'l Appl. . |
| 614079 | 2/1974 | U.S.S.R. . |

OTHER PUBLICATIONS

Yagubov et al., *Azerb. Khim. Zh.* (1984) (5):58:60.
Kozorezov et al., *Zh. Peinr. Khim. (Lenningrad)* (1984) 57(12):2681-2684.
Kozorezov et al., *Neftekhimiya* (1977) 17(3):396–400.
Kozorezov et al., *Neftekhimiya* (1979) 19(3):385-389.
Seapan et al., "Decoking and Regeneration of a Hydrotreating Catalyst by Supercritical Extraction," ACS Symposium Series 411, Ameican Chemical Society, Washington, D.C. (1989).

*Primary Examiner*—Patrick P. Garvin
*Assistant Examiner*—E. D. Irzinski
*Attorney, Agent, or Firm*—Morrison & Foerster

[57] ABSTRACT

This invention is a process for the regeneration of solid acidic hydrocarbon conversion catalysts, but particularly certain transition aluminas and zeolites promoted with Lewis acids (preferably BF$_3$) which have been used in the alkylation of isoparaffins with olefins. The process involves the removal of some portion of the reaction product residue adhering to the solid catalyst by contact with a solvent to partially recover the catalyst's initial activity.

31 Claims, 2 Drawing Sheets

U.S. PATENT DOCUMENTS

| | | |
|---|---|---|
| 3,054,835 | 9/1962 | Hervert et al. |
| 3,054,836 | 9/1962 | Hervert et al. |
| 3,068,301 | 12/1962 | Hervert et al. ................ 585/463 |
| 3,114,785 | 12/1963 | Hervert et al. ................ 585/669 |
| 3,217,062 | 11/1965 | Hervert et al. |
| 3,217,063 | 11/1965 | Hervert et al. |
| 3,220,958 | 11/1965 | Hervert et al. |
| 3,433,747 | 3/1969 | Magee et al. |
| 3,647,916 | 3/1972 | Ceasar et al. ................ 585/722 |
| 3,833,679 | 9/1974 | Gardner et al. ................ 585/749 |
| 3,855,343 | 12/1974 | Huang et al. ................ 585/726 |
| 3,893,942 | 7/1975 | Yang ................ 585/722 |
| 4,028,430 | 6/1977 | Stine et al. ................ 585/722 |
| 4,058,575 | 11/1977 | Cahn et al. ................ 585/374 |
| 4,066,716 | 1/1978 | Herbstman et al. ................ 585/729 |
| 4,243,550 | 1/1981 | Burk et al. ................ 502/24 |
| 4,308,414 | 12/1981 | Madgavkar et al. ................ 585/525 |
| 4,407,731 | 10/1983 | Imai ................ 502/203 |
| 4,427,791 | 1/1990 | Miale et al. ................ 502/203 |
| 4,751,341 | 6/1988 | Rodewald ................ 585/533 |
| 4,914,256 | 4/1990 | Rodewald ................ 585/726 |
| 4,918,255 | 4/1990 | Chou et al. ................ 585/331 |
| 4,935,577 | 6/1990 | Huss, Jr. et al. ................ 585/726 |
| 4,992,614 | 2/1991 | Rodewald ................ 585/722 |
| 4,992,615 | 2/1991 | Huss, Jr. et al. ................ 585/722 |
| 4,992,616 | 2/1991 | Chou et al. ................ 585/722 |

Fig. 2

METHOD FOR REGENERATING CERTAIN ACIDIC HYDROCARBON CONVERSION CATALYSTS BY SOLVENT EXTRACTION

RELATED APPLICATIONS

This is a continuation-in-part of U.S. patent application Ser. No. 07/588,448 to Cooper et al. entitled "ISOPARAFFIN ALKYLATION USING A LEWIS ACID PROMOTED TRANSITION ALUMINA CATALYST" filed Sep. 26, 1990 and now abandoned; Ser. No. 07/697,318 to Cooper et al. entitled "ISOPARAFFIN ALKYLATION USING A LEWIS ACID PROMOTED TRANSITION ALUMINA CATALYST" filed May 7, 1991 and now U.S. Pat. No. 5,157,197; and Ser. No. 07/697,320 to Cooper et al. entitled "LEWIS ACID PROMOTED TRANSITION ALUMINA CATALYSTS SUITABLE FOR ISOPARAFFIN ALKYLATION" filed May 7, 1991 and now abandoned; the entirety of which are incorporated by reference. This application is also related to U.S. patent application Ser. No. 07/718,394 to Rao et al entitled "A METHOD FOR REGENERATING LEWIS ACID-PROMOTED TRANSITION ALUMINA CATALYSTS USED FOR ISOPARAFFIN ALKYLATION BY CALCINATION" filed Jun. 20, 1991; the entirety of which is incorporated by reference.

FIELD OF THE INVENTION

This invention is a process for the regeneration of solid acidic hydrocarbon conversion catalysts, but particularly certain transition aluminas and zeolites promoted with Lewis acids (preferably $BF_3$) which have been used in the alkylation of isoparaffin with olefins. The process involves the removal of some portion of the reaction product residue adhering to the solid catalyst by contact with a solvent to partially recover the catalyst's initial activity.

BACKGROUND OF THE INVENTION

There are a wide variety of hydrocarbon conversion processes using strongly acidic solid acid catalysts at temperatures low enough to maintain the reaction medium in a liquid phase. These processes include oligomerization, alkylation, isomerization, hydroisomerization, etc. The catalysts for these processes include such disparate acidic materials as acidic zeolites, alumina, silica-alumina, silica, boron oxides, phosphorus oxides, titanium oxide, zirconium oxide, chromia, zinc oxide, magnesia, calcium oxide, silica-alumina-zirconia, chromia-alumina, alumina-boria, silica-zirconia, aluminum phosphate molecular sieves, silicoaluminophosphate molecular sieves, solid polymeric ion exchange resins, tetravalent metal phosphonates with pendent acid groups, sulfated metal oxides (such as alumina), and the like. These catalysts may be treated with or complexed with Lewis acids. A side reaction in many of these processes produces what appears to be a low level polymer or oligomer. Unlike many higher temperature processes, the side products are not cokelike in nature. These poorly characterized side reaction products, or "gunk", may be at least partially removed using solvent extraction procedures and carefully chosen solvents. One process, with its concomitant catalyst, to which solvent extraction is especially applicable is isoparaffin/olefin alkylation using solid acid catalysts particularly zeolites or aluminas which have been treated with Lewis acids.

The preparation of high octane blending components for motor fuels using strong acid alkylation processes (notably where the acid is hydrofluoric acid or sulfuric acid) is well-known. Alkylation is the reaction in which an alkyl group is added to an organic molecule (typically an aromatic or olefin). For production of gasoline blending stocks, the reaction is between an isoparaffin and an olefin. Alkylation processes have been in wide use since World War II when high octane gasolines were needed to satisfy demands from high compression ratio or supercharged aircraft engines. The early alkylation units were built in conjunction with fluid catalytic cracking units to take advantage of the light end by-products of the cracking units: isoparaffins and olefins. Fluidized catalytic cracking units still constitute the major source of feedstocks for gasoline alkylation units. In spite of the mature state of strong acid alkylation technology, existing problems with the hydrofluoric and sulfuric acid technologies continue to be severe: disposal of the used acid, unintentional emission of the acids during use or storage, substantial corrosivity of the acid catalyst systems, and other environmental concerns.

Although a practical alkylation process using solid acid catalysts having little or no corrosive components has long been a goal, commercially viable processes do not exist.

The open literature shows several systems used to alkylate various hydrocarbon feedstocks.

The American Oil Company obtained a series of patents in the mid-1950's on alkylation processes involving $C_2$–$C_{12}$ (preferably $C_2$ or $C_3$) olefins and $C_4$–$C_8$ isoparaffins. The catalysts used were $BF_3$-treated solids and the catalyst system (as used in the alkylation process) also contained free $BF_3$. A summary of those patents is found in the following list:

| U.S. Pat. No. | Inventor | $BF_3$-Treated Catalyst* (with free $BF_3$) |
|---|---|---|
| 2,804,491 | May et al. | $SiO_2$ stabilized $Al_2O_3$ (10%–60% by weight $BF_3$) |
| 2,824,146 | Kelly et al. | metal pyrophosphate hydrate |
| 2,824,150 | Knight et al. | metal sulfate hydrate |
| 2,824,151 | Kelly et al. | metal stannate hydrate |
| 2,824,152 | Knight et al. | metal silicate hydrate |
| 2,824,153 | Kelly et al. | metal orthophosphate hydrate |
| 2,824,154 | Knight et al. | metal tripolyphosphate hydrate |
| 2,824,155 | Knight et al. | metal pyroarsenate hydrate |
| 2,824,156 | Kelly et al. | Co or Mg arsenate hydrate |
| 2,824,157 | Knight et al. | Co, Al, or Ni borate hydrate |
| 2,824,158 | Kelly et al. | metal pyroantimonate hydrate salt |
| 2,824,159 | Kelly et al. | Co or Fe molybdate hydrate |
| 2,824,160 | Knight et al. | Al, Co, or Ni tungstate hydrate |
| 2,824,161 | Knight et al. | borotungstic acid hydrate or Ni or Cd borotungstate hydrate |
| 2,824,162 | Knight et al. | phosphomolybdic acid hydrate |
| 2,945,907 | Knight et al. | solid gel alumina (5%–100% by weight of Zn or Cu fluoborate, preferably anhydrous) |

*may be supported on $Al_2O_3$

None of these disclose a process for regenerating an alkylation catalyst using a solvent extraction process for regenerating the catalyst.

Acid catalysts used to oligomerize olefins are known. U.S. Pat. No. 2,748,090 to Watkins suggests the use of a catalyst made up of a Group VIII metal (preferably nickel), a phosphoric acid (preferably containing phosphorus pentoxide), placed on an alumina adsorbent, and pretreated with BF$_3$. Alkylation of aromatics is suggested.

U.S. Pat. No. 2,976,338 to Thomas suggests a polymerization catalyst comprising a complex of BF$_3$ or H$_3$PO$_4$ optionally on an adsorbent (such as activated carbon) or a molecular sieve optionally containing potassium acid fluoride.

Certain references suggest the use of alumina-containing catalysts for alkylation of aromatic compounds. U.S. Pat. No. 3,068,301 to Hervert et al. suggests a catalyst for alkylating aromatics using "olefin-acting compounds". The catalyst is a solid, silica-stabilized alumina up to 10% SiO$_2$, all of which has been modified with up to 100% by weight BF$_3$.

Other BF$_3$-treated aluminas are known. For instance, U.S. Pat. No. 3,114,785 to Hervert et al. suggests the use of a BF$_3$-modified, substantially anhydrous alumina to shift the double bond of 1-butene to produce 2-butene. The preferred alumina is substantially anhydrous gamma-alumina, eta-alumina, or theta-alumina. The various aluminas will adsorb or complex with up to about 19% by weight fluorine depending upon the type of alumina and the temperature of treatment.

In U.S. Pat. No. 4,407,731 to Imai a high surface area metal oxide such as alumina (particularly gamma-alumina, eta-alumina, theta-alumina, silica, or a silica-alumina) is used as a base or support for BF$_3$. The BF$_3$ treated metal oxide is used for generic oligomerization and alkylation reactions. The metal oxide is treated in a complicated fashion prior to being treated with BF$_3$. The first step entails treating the metal oxide with an acid solution and with a basic aqueous solution. The support is washed with an aqueous decomposable salt such as ammonium nitrate. The support is washed using deionized H$_2$O until the wash water shows no alkali or alkaline earth metal cations in the filtrate. The support is dried and calcined. The disclosure suggests generically that BF$_3$ is then introduced to the treated metal oxide support. The examples show introduction of the BF$_3$ at elevated temperatures, e.g, 300° C. or 350° C.

Similarly, U.S. Pat. No. 4,427,791 to Miale et al. suggests the enhancement of the acid catalytic activity of inorganic oxide materials (such as alumina or gallia) by contacting the material with ammonium fluoride or boron fluoride, contacting the treated inorganic oxide with an aqueous ammonium hydroxide or salt solution, and calcining the resulting material. The inorganic oxides treated in this way are said to exhibit enhanced Brönsted acidity and, therefore, is said to have improved acid activity towards the catalysis of numerous and several reactions (such as alkylation and isomerization of various hydrocarbon compounds). A specific suggested use for the treated inorganic oxide is as a matrix or support for various zeolite materials ultimately used in acid catalyzed organic compound conversion processes.

U.S. Pat. No. 4,751,341 to Rodewald shows a process for treating a ZSM-5 type zeolite with BF$_3$ to reduce its pore size, enhance its shape selectivity, and increase its activity towards the reaction of oligomerizing olefins. The patent also suggests using these materials for alkylation of aromatic compounds.

Certain Soviet publications suggest the use of Al$_2$O$_3$ catalysts for alkylation processes. Benzene alkylation using those catalysts (with 3 ppm to 5 ppm water and periodic additions of BF$_3$) is shown in Yagubov, Kh. M. et al., *Azerb. Khim. Zh.*, 1984, (5) p. 58. Similarly, Kozorezov, Yu and Levitskii, E. A., *Zh. Prikl. Khim.* (*Leningrad*), 1984, 57 (12), p. 2681, show the use of alumina which has been treated at relatively high temperatures and modified with BF$_3$ at 100° C. There are no indications that BF$_3$ is maintained in excess. Isobutane alkylation using Al$_2$O$_3$/BF$_3$ catalysts is suggested in *Neftekhimiya*, 1977, 17 (3), p. 396; 1979, 19 (3), P. 385. The olefin is ethylene. There is no indication that BF$_3$ is maintained in excess during the reaction. The crystalline form of the alumina is not described nor is any method suggested for regeneration of the catalysts.

U.S. Pat. No. 4,918,255 to Chou et al. suggests a process for the alkylation of isoparaffins and olefins using a composite described as "comprising a Lewis acid and a large pore zeolite and/or a non-zeolitic inorganic oxide". The process disclosed requires isomerization of the olefin feed to reduce substantially the content of alpha-olefin and further suggests that water addition to the alkylation process improves the operation of the process.

U.S. Pat. No. 4,992,616 to Chou et al. deals with the process noted above for alkylation of isoparaffins and olefins using a composite described as "comprising a Lewis acid and a large pore zeolite" but requires addition of water for improving the operation of the process. The best Research Octane Number (RON) product shown in the examples and made using the disclosed invention is 86.0 (Table 2).

Similarly, PCT published applications WO 90/00533 and 90/00534 (which are based in part on the U.S. patent to Chou et al. noted above) suggest the same process as does Chou et al. WO 90/00534 is specific to a process using boron trifluoride-treated inorganic oxides including "alumina, silica, boria, oxides of phosphorus, titanium oxide, zirconium oxide, chromia, zinc oxide, magnesia, calcium oxide, silica-alumina-zirconia, chromia-alumina, alumina-boria, silica-zirconia, and the various naturally occurring inorganic oxides of various states of purity such as bauxite, clay and diatomaceous earth". Of special note is the statement that the "preferred inorganic oxides are amorphous silicon dioxide and aluminum oxide". The examples show the use of amorphous silica (and BF$_3$) to produce alkylates having an RON of no greater than 94. U.S. Pat. No. 4,935,577 to Huss, Jr. et al. teaches a process for the catalytic distillation of various hydrocarbons by e.g., alkylation or oligomerization, using a catalyst "consisting essentially of a Lewis acid promoted inorganic oxide." The inorganic oxide may be selected from the non-zeolitic materials discussed above with regard to the Chou et al. published PCT applications. Additionally, the inorganic oxide may be a large pore crystalline molecular sieve.

There are a variety of disclosed ways to regenerate catalysts used in alkylation processes or using Lewis acids. Typical of such processes are the following.

U.S. Pat. No. 3,647,916, to Caesar et al. shows a process for isoparaffin-olefin alkylation using crystalline zeolite catalysts at low isoparaffin to olefin ratios. The zeolite is first steamed to reduce the number of acid sites and so reduce the amount of olefin polymerization which occurs. The isoparaffin is added to the catalyst before the olefin is introduced to further limit the amount of polymerization. There is no discussion of the use of auxiliary Lewis acids in conjunction with the zeolites. Nevertheless, the catalysts are susceptible to deactivation due to the "accumulation in the pores thereof of olefin polymerization products". The regeneration is carried out by burning the surface residue "in an oxygen-containing atmosphere at an elevated temperature in the range of about 800° to 1400° F." followed by a step in which the catalyst is contacted with an aromatic or polar solvent.

U.S. Pat. No. 3,833,679 to Gardner et al. shows a paraffin isomerization process using an $HSbF_6$ catalyst supported on a fluorided alumina. The catalyst was regenerated by introduction of an HF stream sufficient to convert to any $SbF_5$ to $HSbF_6$. No mention is made of removal of any hydrocarbonaceous materials from the catalyst using this treatment.

U.S. Pat. No. 3,893,942 to Yang also shows a process for isoparaffin-olefin alkylation using crystalline zeolite catalysts. A small amount of a hydrogenation catalyst (Group VIII metal) is included in the zeolite. Hydrogen gas is periodically introduced into the zeolite (apparently after the catalyst has been partially deactivated) and restores the activity of the catalyst. Yang indicates that the nature of the chemical reaction between the hydrocarbonaceous deposit and the hydrogen is not clear but hydrogen is consumed and the alkylation activity is restored. This procedure is said to avoid "refractory coke deposits" formed when using high temperature inert gas regeneration treatments. Oxidative treatments are then said to be necessary. A paraffinic wash is desirably first applied to the catalyst to assist in the following hydrogenation step.

U.S. Pat. No. 3,855,343 to Huang et al. teaches an isoparaffin-olefin alkylation process in which the catalyst is a combination of a macroreticular acid cation exchange resin and boron trifluoride. The boron trifluoride is present in an amount in excess of that needed to saturate the resin. This catalyst is said to "age" and after some period of time must be regenerated. The catalyst is regenerated by solvent extraction with a polar solvent, preferably a low molecular weight alcohol.

The process disclosed in U.S. Pat. No. 4,058,575 to Cahn et al. is a method of converting hydrocarbons, e.g., by alkylating them, in the presence of a Lewis acid and a strong Brönsted acid. Partially deactivated catalytic materials are pretreated with a hydrocarbon to remove contaminants and deactivated catalyst species.

The U.S. Pat. No. 4,308,414 to Madgavkar shows a process for oligomerizing longer alpha-olefins using a particulate adsorbent (preferably $SiO_2$) and adsorbed boron trifluoride and water. The catalyst is regenerated by the procedure of adding a small amount of water with the feed olefin.

The U.S. Pat. Nos. 4,914,256 and 4,992,614 to Rodewald suggest the reactivation of catalysts (particularly supported boron trifluoride-containing alkylation catalysts) used in a variety of hydrocarbon conversion catalysts by application of ultrasonic energy to the partially deactivated catalyst. The process is said to eliminate the need for separation of the catalyst from the feedstock nor to subject the catalyst to a "burn-off" operation.

One disclosure showing the use of $SO_2$ to regenerate catalysts is Seapan et al, "Decoking and Regeneration of a Hydrotreating Catalyst by Supercritical Extraction", ACS Symposium Series 411, American Chemical Society, Washington, D.C., 1989. This disclosure shows the use of $SO_2$ (and other solvents) at pressures above their critical pressures to remove coke-type carbon species from hydrotreating catalysts. The use of $SO_2$ above 1200 psig is shown. The disclosure does not suggest the treatment of any catalysts which have non-coke residue.

These disclosures do not show the use of our liquid solvent extraction process to revive acidic catalysts having non-coke residue and especially those which are promoted with a Lewis acid (preferably $BF_3$) and which have been used in the alkylation of isoparaffin with olefins.

SUMMARY OF THE INVENTION

This invention is a solvent extraction process for the regeneration of solid acidic hydrocarbon conversion catalysts but particularly those acidic catalysts such as aluminas or zeolites which have been promoted with Lewis acids (preferably $BF_3$) and used in the alkylation of isoparaffins with olefins. The process involves contacting the solid acidic catalyst with a liquid solution comprising a solvent selected from $SO_2$; oxygenates such as $C_1$–$C_4$ alcohols, ketones, and aldehydes; nitriles such as acetonitrile; and phenolics such as anisole and phenol. When the solid acidic catalyst additionally comprises a Lewis acid the process involves contacting the combination catalyst with a liquid solution comprising a solvent selected from $SO_2$ or from aromatic ethers and phenolics such as anisole and phenol.

The catalysts for these processes include such disparate acidic materials as acidic zeolites, alumina, silica-alumina, silica, boron oxides, phosphorus oxides, titanium oxide, zirconium oxide, chromia, zinc oxide, magnesia, calcium oxide, silica-alumina-zirconia, chromia-alumina, alumina-boria, silica-zirconia, aluminum phosphate molecular sieves, silicoaluminophosphate molecular sieves, solid polymeric ion exchange resins, tetravalent metal phosphonates with pendent acid groups, sulfated metal oxides (such as alumina), and the like. These catalysts may be treated with or complexed with Lewis acids. They are all acidic in their functionality as hydrocarbon conversion catalysts.

The alkylation process in which certain of the candidate catalysts are used produces alkylates suitable for use as very high octane, non-aromatic blending components in motor fuels. The alkylates are produced from olefins and isoparaffins. The catalyst used comprises one or more transitional aluminas which are treated with at least one Lewis acid, preferably $BF_3$. The process optimally utilizes an amount of free Lewis acid and produces high octane alkylate.

The regeneration process includes the steps of separating the solid component from the liquid reaction medium (but preferably maintaining it in the substantial absence of oxygen and water) and contacting the solid with an excess of the liquid solvent. The catalyst may be heated at a lower temperature prior to the solvent contact step so to volatilize certain hydrocarbons and to recover any complexed Lewis acid or may be washed with an inert solvent such as isobutane or other branched alkane.

DESCRIPTION OF THE INVENTION

This invention is a solvent extraction process for the regeneration of solid acidic hydrocarbon conversion catalysts but particularly those acidic catalysts such as aluminas or zeolites which have been promoted with Lewis acids (preferably $BF_3$) and used in the alkylation of isoparaffins with olefins. The process involves contacting the solid acidic catalyst (which does not contain a significant Lewis acid component) with a liquid solution comprising a solvent selected from $SO_2$; oxygenates such as $C_1-C_4$ alcohols, ketones, and aldehydes; nitriles such as acetonitrile; and phenolics such as anisole and phenol. When the solid acidic catalyst additionally comprises a Lewis acid, the process involves contacting the combination catalyst with a liquid solution comprising a solvent selected from $SO_2$ or from aromatic ethers and phenolics such as anisole and phenol.

The solid acid catalysts suitable for regeneration using these processes include such disparate acidic materials as acidic zeolites, alumina, silica-alumina, silica, boron oxides, phosphorus oxides, titanium oxide, zirconium oxide, chromia, zinc oxide, magnesia, calcium oxide, silica-alumina-zirconia, chromia-alumina, alumina-boria, silica-zirconia, aluminum phosphate molecular sieves, silicoaluminophosphate molecular sieves, solid polymeric ion exchange resins, tetravalent metal phosphates with pendent acid groups, sulfated metal oxides (such as alumina), and the like. In particular, the zeolites are preferably large pore zeolitic materials such as zeolite L, zeolite X, zeolite Y, ZSM-4, ZSM-5, ZSM-11, ZSM-12, zeolite $\beta$, zeolite $\Omega$, mordenite, and faujasite. The zeolites must be acidic but may be natural, synthetic, or may have framework substitutions of other metals. These catalysts may be treated with or complexed with Lewis acids. They are all acidic in their functionality as hydrocarbon conversion catalysts.

The preferred catalyst system for this regeneration process comprises certain transition aluminas which have been treated with one or more Lewis acids in combination with a minor amount of free Lewis acid. The alumina catalyst component is made by contacting free Lewis acid with certain transition alumina substrates.

The Alumina Catalyst Component

The preferred alumina catalyst component comprises or consists essentially of a major amount of transition aluminas (preferably eta- or gamma-alumina) which has been treated with a Lewis acid, preferably $BF_3$. The catalyst component is acidic in nature and contains substantially no metals (except, of course, aluminum and the semi-metal boron) in catalytic amounts except as may be present in trace amounts in the $BF_3$ or alumina.

Alumina

Aluminum oxide (alumina) occurs abundantly in nature, usually in the form of a hydroxide in the mineral bauxite, along with other oxidic impurities such as $TiO_2$, $Fe_2O_3$, and $SiO_2$. The Bayer process is used to produce a reasonably pure $Al_2O_3$ having a minor amount of $Na_2O$. The Bayer process $Al_2O_3$ is further treated to produce a variety of alumina hydroxides:

| Material | Common Name | % $H_2O$ | $H_2O/Al_2O_3$ | CAS Index No. |
|---|---|---|---|---|
| α-trihydrate | hygrargillite/gibbsite | 35 | 3.0 | 14762-493 |
| β-trihydrate | bayerite | 35 | 3.0 | 20257-20-9 or 12252-72-1 |
| β-trihydrate | nordstrandite | 35 | 3.0 | 13840-05-6 |
| α-monohydrate | boehmite | 15 | 1.0 | 1318-23-6 |
| hydrate | psuedoboehmite | 26 | 2.0 | — |

The aluminum hydroxides may then be treated by heating to produce various activated or transition aluminas. For instance, the aluminum hydroxide known as boehmite may be heated to form a sequence of transition phase aluminas: gamma, delta, theta, and finally, alpha (see Wefers et al., "Oxides and Hydroxides of Alumina", Technical Paper No. 19, Aluminum Company of America, Pittsburgh, Pa., 1972, pp. 1-51).

Transition aluminas (and their crystalline forms) include:

| | |
|---|---|
| gamma | tetragonal |
| delta | orthorhombic/tetragonal |
| eta | cubic |
| theta | monoclinic |
| chi | cubic/hexagonal |
| kappa | hexagonal |
| lambda | orthorhombic |

Activated aluminas and aluminum hydroxides are used in various chemical processes as catalyst and adsorbents. The aluminas suitable for use in this process include the noted transition aluminas: gamma, delta, eta, theta, chi, kappa, rho, or lambda. Especially preferred are gamma- and eta-aluminas. Mixtures of the two are also desirable.

Since it is difficult to produce a substantially pure single phase transition alumina, mixtures of various aluminas are tolerable. For instance, in the production of eta-alumina, gamma-alumina is often concurrently present in the resulting product. Indeed, x-ray diffraction analysis can only detect the difference between the two phases with some difficulty. Aluminum hydroxides (boehmite, gibbsite, etc.) may be present in the predominately transition phase product in more than trivial amounts so long as they do not substantially affect the desired alkylation reaction.

The catalyst may be found in any appropriate form such as pellet, granules, bead, sphere, powder, or other shape to facilitate its use in fixed beds, moving beds, or fluidized beds.

Lewis Acids

If the catalyst system of the regeneration process uses one or more Lewis acids in conjunction with the acidic catalyst noted above, then the Lewis acids may one of those described below.

A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentachloride ($SbF_5$); aluminum halides ($AlCl_3$ and $AlBr_3$); titanium halides such as $TiBr_4$, $TiCl_4$, and $TiCl_3$; zirconium tetrachloride ($ZrCl_4$); phosphorus pentafluoride ($PF_5$); iron halides such as $FCl_3$ and $FeBr_3$; and the like. Weaker Lewis acids such as tin, indium, bismuth, zinc, or mercury halides are also acceptable.

Catalyst Preparation

The preferred alumina catalyst system may be prepared in situ in an alkylation reactor by passing the Lewis acid in gaseous form through the vessel containing the transition alumina. Alternatively, the alumina may be contacted with the Lewis acid and later introduced into the reactor. In any case, the alumina should be substantially dry prior to contact with the Lewis acid and maintained in that state. Contact temperatures between −25° C. and about 100° C. are acceptable; a temperature between −25° C. and 30° C. is preferred. The partial pressure of gaseous Lewis acid added to the alumina is not particularly important so long as a sufficient amount of Lewis acid is added to the alumina. We have found that treatment of the alumina with $BF_3$ at the noted temperatures will result in an alumina-$BF_3$ complex containing $BF_3$ sufficient to carry out the alkylation. The alumina contains between 0.5% and 30% by weight of $BF_3$.

Obviously, the alumina or other catalyst may be incorporated into a binder prior to its treatment with Lewis acid. The binders may be clays (such as montmorillonite and kaolin) or silica based materials (such as gels or other gelatinous precipitates). Other binder materials include carbon and metal oxides such as alumina, silica, titania, zirconia, and mixtures of those metal oxides. The composition of the binders is not particularly critical but care must be taken that they not substantially interfere with the operation of the alkylation reaction.

Alkylation Process

The alkylation process used in one aspect of the invention involves contacting an isoparaffin with an olefin in the presence of the alumina-based catalyst discussed above and in the presence of some excess free Lewis acid.

Specifically, the catalyst of this invention is active at low temperatures (as low as −30° C.) as well as at higher temperatures (nearing 50° C.). Lower temperatures (−5° C. to 15° C.) are preferred because of the enhanced octane of the alkylate produced and are particularly preferred if the feedstream contains more than about 1% isobutylene. Higher temperatures also tend to produce larger amounts of polymeric materials. The pressure used in the alkylation process is not particularly critical. In general, the pressure must be kept high enough to maintain the reactants and products in the liquid phase, although the catalyst will produce alkylation products when the feedstock is gaseous. As a practical guideline, the process may be operated at atmospheric pressure to about 750 psig. The amount of catalyst used in the alkylation process depends upon a wide variety of disparate variables. Nevertheless, we have found that the Weight Hourly Space Velocity ("WHSV" = weight of olefin feed/hour ÷ weight of catalyst) may effectively be between 0.1 and 120, especially between 0.5 and 30. The overall molar ratio of isoparaffin to olefin is between about 1.0 and 50.0. Preferred ranges include 2.0 and 25.0; the more preferred include 3.0 and 12.0.

The feedstreams introduced into the catalyst desirably comprise isoparaffins having from four to ten carbon atoms and, most preferably, four to six carbon atoms. Isobutane is most preferred because of its ability to make high octane alkylate. The olefins desirably contain from three to five carbon atoms, i.e., propylene, cis- and trans-butene-2, butene-1, and amylenes.

The products of this alkylation process typically contain a complex mixture of highly branched alkanes. For instance, when using isobutane as the alkane and n-butylene as the olefin, a mixture of 2,2,3-; 2,2,4-; 2,3,3-; and 2,3,4-trimethylpentane (TMP) will result often with minor amounts of other isomeric or polymeric products.

The process involved may utilize the catalyst in a fixed bed using single or multiple feeds. That is to say, the feedstocks may be independently introduced at one or more points throughout the bed or between multiple beds. Desirably, the catalyst is contacted with the feedstocks in one or more of continuously stirred reactors, preferably with feed to each reactor.

Regeneration Step

As we have discussed above, the regeneration step involves the steps of separating the solid catalytic material from the product of the hydrocarbon conversion process by use of a liquid-solid separation technique and followed by the step of contacting the catalytic material with a solvent capable of regenerating the material. The solvent desirably is selected from $SO_2$; oxygenates such as $C_1$-$C_4$ alcohols, ketones, and aldehydes; alkylnitriles such as acetonitrile; and phenolics and aromatic ethers such as anisole and phenol. Most preferably, the solvent comprises $SO_2$.

The catalyst may be first contacted with an inert gas to strip any excess gaseous Lewis acid and light hydrocarbons from the solid catalyst component. The catalyst may also be treated using a mild heating step (e.g., 50° to 75° C.) prior to the solvent contact step to further strip hydrocarbons from the solid. Additionally, the removal of hydrocarbons and excess Lewis acid may be facilitated by contact with an inert gas such as helium, nitrogen, etc. The hydrocarbons and Lewis acid may be recycled as appropriate.

The process involves contacting the solid acidic catalyst with a liquid solution comprising a solvent selected form $SO_2$; oxygenates such as $C_1$-$C_4$ alcohols, ketones, and aldehydes; nitriles such as acetonitrile; and phenolics such as anisole and phenol. When the solid acidic catalyst additionally comprises a Lewis acid the process involves contacting the combination catalyst with a liquid solution comprising a solvent selected from $SO_2$ or from aromatic ethers and phenolics such as anisole and phenol.

Specifically, the regeneration step involves the contacting of the solid catalyst component with the liquid solvent stream. Clearly, the choice made for the step of physically contacting the catalyst is dependent in large part upon the specifics of the catalyst component itself. For instance, if the catalyst is in the form of tablets or extrudates or Pall rings (or the like) and are found in a fixed bed, the most appropriate way to contact the catalyst would be to pass the liquid solvent over the catalyst in the catalyst's fixed bed. If, the catalyst is used as a slurry, the catalyst may be transported to a vessel suitable for contacting the alumina component with a liquid stream and then separating the solid from the liquid. The reactor in such a process would likely be a good choice for such a vessel. We have found it to be desirable that the catalyst be kept out of contact with water and with oxygen.

The amount of solvent used should be sufficient to remove at least a portion of the reaction residue found on the catalyst component. The residue is ill-defined but often appears to be a moderately long-chained or polymeric material largely alkane in nature but with a minor olefinic character. The residues also often contain polyolefins and aromatic components in small concentrations. We do not consider this regeneration process to be appropriate for residue caused as a result of high temperature hydrocarbon conversion processes, at least those which produce graphitic or carbonaceous residues on the catalyst. Such residues typically have H/C ratios less than one. Although the amount is not believed to be critical, we have found that for most alumina-based alkylation catalysts, an amount of about 100 gm. of solvent per gm. of catalyst is sufficient to regenerate the catalyst to at least 40% of the prior activity.

The temperature of the contact step is also not critical but for alkylation catalysts, treatment in the range of 0° C. to 50° C. is appropriate.

When a solvent comprising $SO_2$ is utilized in the contact step to regenerate catalysts containing Lewis acids, the solvent should be generally dry; preferably it is substantially free of organic and inorganic bases and $SO_3$ and $H_2SO_4$. The level of these contaminants may be such that they do not substantially affect the level of catalyst activity upon return to the hydrocarbon conversion medium. Hydrocarbonaceous diluents, such as are the products of the accompanying hydrocarbon conversion process often make suitable diluents for the solvent used to regenerate the catalyst.

Once the steps outlined above are completed, the solid catalyst component may be again be treated with one or more Lewis acids as specified above and returned to the hydrocarbon conversion step. It may be desirable when using $SO_2$ as the solvent and a gaseous Lewis acid to overpressure the gaseous Lewis acid (e.g., at a pressure above the pressure at which the reaction and/or the solvent treatment step is carried out) before returning the catalyst to service; although we do not wish to be bound by this theory, we believe that the overpressure aids in sweeping or displacing the solvent from the catalyst surface.

The invention has been disclosed by direct description. Below may be found examples showing various aspects of the invention. The examples are only examples of the invention and are not to be used to limit the scope of the invention in any way.

EXAMPLES

EXAMPLE 1

This example shows the regeneration of an alumina-based catalyst which had been treated with $BF_3$ and then used with excess $BF_3$ in an alkylation reaction. The feedstream to the alkylation step was a synthetically prepared feed simulating the hydroisomerized $C_4$ effluent from an MTBE unit (MTBE effluent).

The olefinic feedstock was prepared containing (by weight) 94% trans- and cis-2-butene, 5% butene-1, and 1% isobutylene. The feedstock was prepared by mixing the olefinic feedstock with isobutane such that the final molar ratio of isobutane to olefin was 6/1. This was fed to the alkylation reactor at a weight hourly space velocity (WHSV—based on olefin) was 10.7. The reaction temperature was held to 0° C. Samples were periodically removed from the reactor for analysis by gas-liquid chromatography.

During each reaction step, the alkylation reaction was run until approximately 85 gm of olefin per gram of catalyst (i.e., the catalyst "age") had been processed. At that point, there was some indication of a loss of activity of the catalyst as evidenced by a decreasing amount of product $C_8$ content and a concomitant increase in the product $C_{12}^+$ content. Additionally, a decrease in the (R+M)/2 as calculated from the gas-liquid chromatography data using well-known correlations (Hutson and Logan, "Estimate Alky Yield and Quality", Hydrocarbon Processing, September, 1975, pp. 107-108) was noted at about that catalyst age.

The catalyst was then regenerated using the following procedure:
1. 50 cc of isobutane were added to the alkylation reactor primarily to raise the liquid level to assist in washing back into solution any catalyst that had accumulated at the top of the reactor,
2. the liquid product and isobutane were removed from the reactor through a filtering frit using pressurized inert gas,
3. the reactor containing the spent catalyst was purged with inert gas at 15 cc/min for thirty minutes until the catalyst had the consistency of a free-flowing powder,
4. 150 ml. $SO_2$ were added to the reactor and the contents stirred for 20 minutes,
5. $SO_2$ was withdrawn from the reactor using pressurized inert gas and recovered in a collection vessel. The flow of inert gas was continued until no liquid was present in the reactor,
6. steps 4 and 5 were repeated twice,
7. the system was flused with flowing inert gas for 15 minutes at 15 cc/min.,
8. $BF_3$ was added to the reactor vessel containing the regenerated catalyst and pressurized to a total pressure of 60 psig of $BF_3$. This pressure was held for 15 minutes. The reactor was then depressurized and purged with inert gas for five minutes, and
9. step 8 was repeated with the exception that following the depressurization of the $BF_3$, the inert gas was allowed to purge the system for 20 minutes. The system was then ready for the next alkylation cycle.

Following regeneration, the same procedure to initiate the alkylation reaction was followed as with a fresh catalyst, with the exception that isobutane was added to the reactor containing the catalyst and stirred for approximately 30 minutes prior to addition of the $BF_3$. This was to insure that the catalyst was well mixed into the liquid medium.

The described procedures of alkylation followed by regeneration were repeated for a total of nine cycles.

Figure 1:
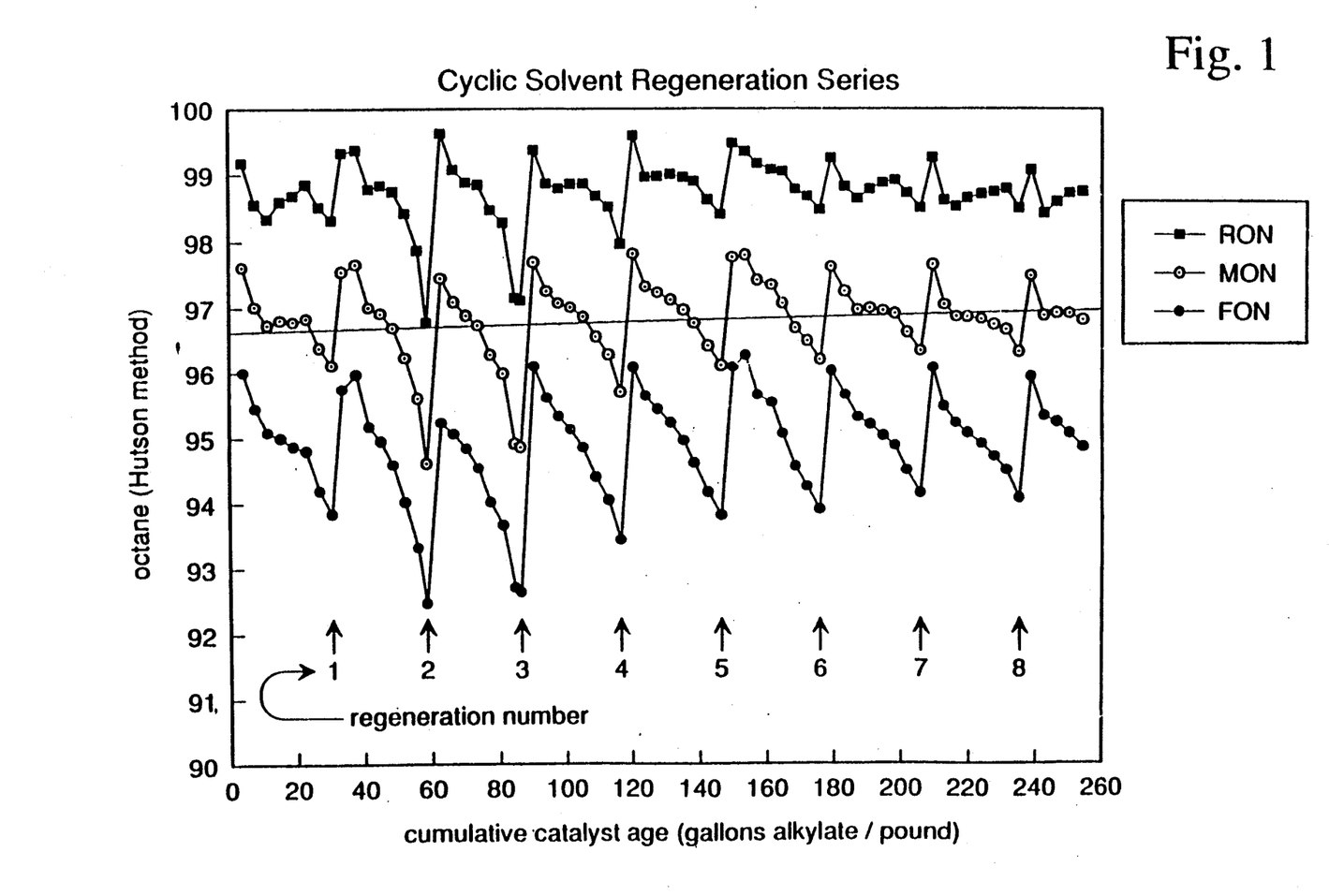
FIG. 1 is a graph of the results of the regeneration procedure of the invention as practiced in Example 1 upon an alumina-based alkylation catalyst over several liquid $SO_2$ regeneration cycles.

The results of the product analysis from each cycle are summarized in Table 1 and FIG. 1, indicating initial and final performance as measured by gas chromatographic analysis of the hydrocarbon effluent. The data clearly show that the full activity of the catalyst is restored using the regeneration procedure.

Following the final alkylation cycle, the catalyst was again regenerated with $SO_2$ using the noted procedure. Analysis of the recovered catalyst by elemental analysis gave the following results:

| | |
|---|---|
| Carbon, wt % | 0.3 |
| Boron, wt % | 1.9 |
| Fluorine, wt % | 11.1 |
| Sulfur, wt % | (below detection limits) |

Figure 2:
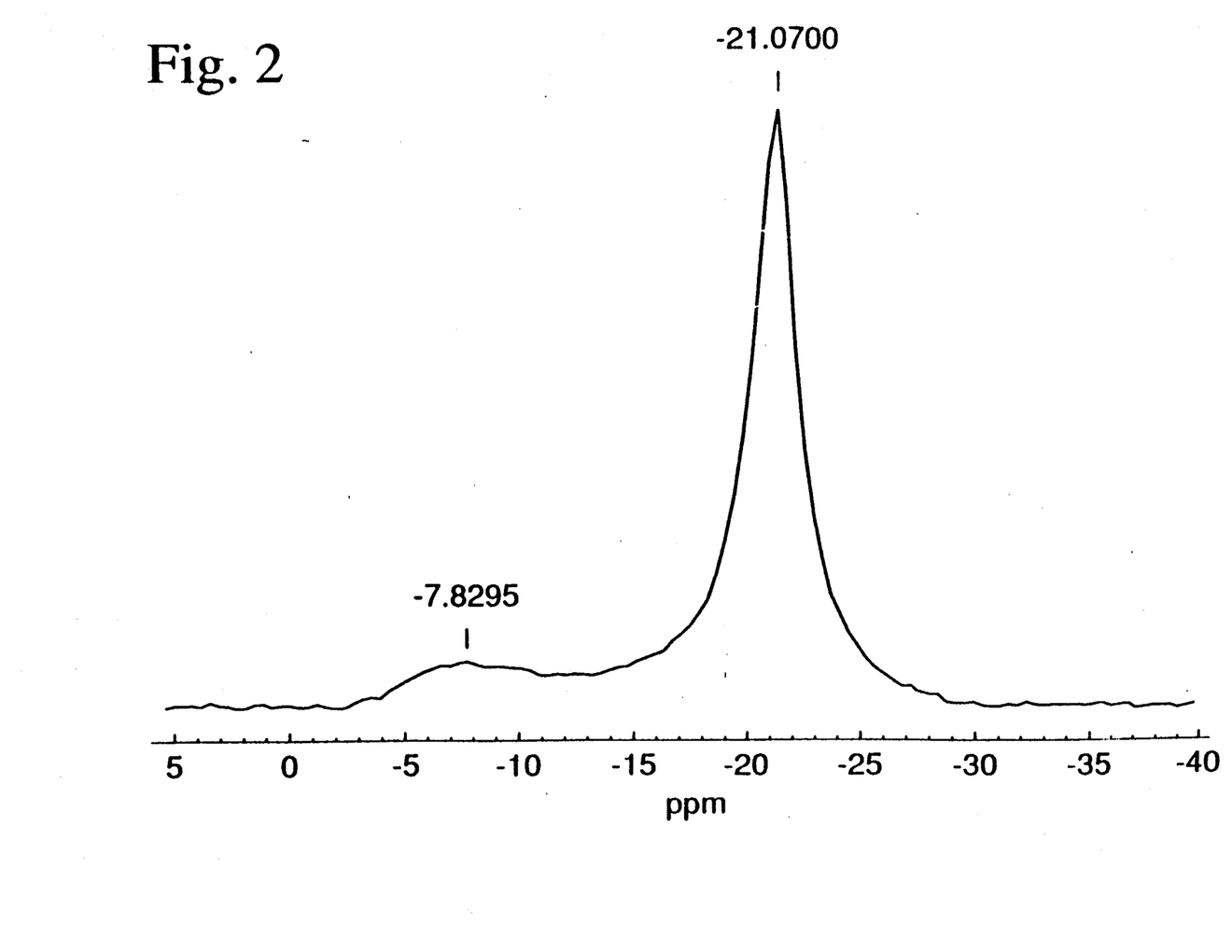
FIG. 2 is an $^{11}B$ NMR graph of the catalyst used in Example 1 following several regeneration cycles.

The low carbon and sulfur content of the catalyst show that the $SO_2$ regeneration procedure is very efficient. The $SO_2$ does not accumulate on the surface of the catalyst after regeneration. The boron and fluorine contents of the catalyst are very similar to that found on a fresh catalyst. Analysis of the boron-containing species by solid state NMR of boron (FIG. 2) shows a single resonance peak at about $-21$ ppm, indicating the presence of a sole active boron species and the absence of any decomposition products arising from the regeneration procedure. Thus, the regeneration procedure is believed to remove contaminating carbon residues while maintaining intact the important species on the catalyst surface.

TABLE 1

| Cycle # | | C₈, wt % | C₁₂⁺, wt % | Octane, (R + M)/2 |
|---|---|---|---|---|
| 1 | initial | 95.3 | 2.4 | 97.6 |
|   | final   | 92.2 | 4.9 | 96.1 |
| 2 | initial | 95.3 | 2.6 | 97.6 |
|   | final   | 85.8 | 9.8 | 94.6 |
| 3 | initial | 96.8 | 2.0 | 97.5 |
|   | final   | 87.4 | 8.9 | 94.9 |
| 4 | initial | 95.4 | 2.2 | 97.7 |
|   | final   | 90.9 | 6.5 | 95.7 |
| 5 | initial | 96.1 | 1.7 | 97.8 |
|   | final   | 92.4 | 5.0 | 96.1 |
| 6 | initial | 95.8 | 2.1 | 97.8 |
|   | final   | 93.5 | 4.4 | 96.2 |
| 7 | initial | 95.1 | 2.8 | 97.7 |
|   | final   | 93.4 | 4.5 | 96.3 |
| 8 | initial | 94.9 | 2.9 | 97.7 |
|   | final   | 93.4 | 4.3 | 96.3 |
| 9 | initial | 94.3 | 3.1 | 97.5 |

EXAMPLE 2

This example demonstrates the SO₂ regeneration step using a commercial MTBE raffinate feedstock which had been hydroisomerized to remove butadiene and to convert a portion of the butene-1 to cis- and trans-2-butene-2. This feedstock has the following composition (in wt % on a total olefin basis): 4.3% isobutene, 4.9% butene-1, 87.2% cis- and trans-butene-2, 1.9% 2-methyl butene-1 and 2-methyl butene-2, and 1.7% pentene-2.

This olefinic feedstock was blended with isobutane to a final isobutane/olefin ratio of 6. Normal butane was added to produce a level of 18% in the total feed. This feedstock was fed to the catalyst at 0° C. at a WHSV (on olefin) of 7.2. Samples were taken periodically and analyzed by gas chromatography.

The catalyst was run for a total of five cycles with regeneration between cycles using liquid SO₂ in the procedure shown in Example 1. The C₈, C₁₂⁺, and (R+M)/2 values measured at the beginning and at the end of each cycle are shown in Table 2. This example shows that the regeneration step using SO₂ performs well on an alkylation catalyst which has been used on a commercial feed.

TABLE 2

| Cycle # | | C₈ | C₁₂⁺ | Octane, (R + M)/2 |
|---|---|---|---|---|
| 1 | initial | 77.0 | 6.6  | 95.3 |
|   | final   | 40.4 | 26.4 | 85.9 |
| 2 | initial | 79.7 | 6.8  | 95.6 |
|   | final   | 37.9 | 22.3 | 85.1 |
| 3 | initial | 81.5 | 6.0  | 95.5 |
|   | final   | 60.5 | 15.3 | 91.5 |
| 4 | initial | 79.7 | 5.5  | 95.7 |
|   | final   | 67.7 | 17.2 | 92.2 |
| 5 | initial | 82.8 | 4.5  | 95.8 |

It should be clear that one having ordinary skill in this art would envision equivalents to the processes found in the claims that follow and that those equivalents would be within the scope and spirit of the claimed invention.

We claim as our invention:

1. A method for regenerating an acidic alumina, solid, hydrocarbon conversion catalyst which has been used in the alkylation of isoparaffin with olefins, wherein said hydrocarbon conversion catalyst does not contain a significant Lewis acid component, the method comprising the steps of:
   a. separating the acidic alumina, solid, hydrocarbon conversion catalyst from a hydrocarbon conversion reaction medium,
   b. contacting the acidic alumina, solid, hydrocarbon conversion catalyst with a liquid solution comprising a solvent selected from the group consisting of $SO_2$, $C_1$-$C_4$ alcohols, $C_1$-$C_4$ ketones, $C_1$-$C_4$ aldehydes, acetonitrile, anisole and phenol, and
   c. separating the catalyst component from the solvent.

2. The process of claim 1 where the solvent comprises $SO_2$.

3. The process of claim 1 additionally comprising the step of heating the solid catalyst to a temperature of up to about 75° C. after the separation step to substantially remove volatile hydrocarbons.

4. A method for regenerating an acidic, solid, hydrocarbon conversion catalyst additionally containing a Lewis acid component comprising the steps of:
   a. separating the acidic, solid, hydrocarbon conversion catalyst from a hydrocarbon conversion reaction medium,
   b. contacting the acidic, solid, hydrocarbon conversion catalyst with a liquid solution comprising a solvent selected from the group consisting of $SO_2$, anisole, and phenol, and
   c. separating the catalyst component from the solvent.

5. The process of claim 4 where the catalyst is selected from acidic zeolites, alumina, silica-alumina, silica, aluminum phosphate molecular sieves, silicoaluminophosphate molecular sieves, solid polymeric ion exchange resins, tetravalent metal phosphonates with pendent acid groups, and sulfated metal oxides.

6. The process of claim 5 where the catalyst is selected from zeolites, alumina, silica-alumina, and silica.

7. The process of claim 6 where the catalyst is alumina.

8. The process of claim 5 where the catalyst comprises a strong Lewis acid selected from BF3, BCl3, BBr3, Bl3, SbF5, AlCl3, AlBr3, TiBr4, TiCl4, TiCl3, ZrCl4, PF5, FeCl3, and FeBr3.

9. The process of claim 8 where the strong Lewis acid is selected from SbF5, AlCl3, and BF3.

10. The process of claim 9 where the strong Lewis acid is BF3.

11. The process of claim 5 where the solvent comprises $SO_2$.

12. The process of claim 4 additionally comprising the step of heating the solid catalyst to a temperature of up to about 75° C. after the separation step to substantially remove volatile hydrocarbons.

13. A method for regenerating an alkylation catalyst component which component comprises a major amount of a transition alumina which has been contacted with a strong Lewis acid to produce an alkylation catalyst component containing between 0.5% and 30% by weight of Lewis acid and has been partially deactivated by use in an alkylation reaction medium, comprising the steps of:
   a. separating the alkylation catalyst from the alkylation reaction medium,
   b. contacting the alkylation alumina catalyst component with a solvent comprising $SO_2$, and c. separating the alkylation alumina catalyst component from the $SO_2$ solvent.

14. The process of claim 13 where the transition alumina is selected from gamma-alumina, eta-alumina, theta-alumina, chi-alumina, kappa-alumina, lambda-alumina, rho-alumina, and mixtures.

15. The process of claim 14 where the transition alumina is selected from gamma-alumina, eta-alumina, and mixtures.

16. The process of claim 13 where the strong Lewis acid is selected from $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$, and $FeBr_3$.

17. The process of claim 16 where the strong Lewis acid is selected from $SbF_5$, $AlCl_3$, and $BF_3$.

18. The process of claim 17 where the strong Lewis acid is $BF_3$.

19. The process of claim 13 additionally comprising the step of heating the alkylation catalyst component to a temperature of up to about 75° C. after the separation step to substantially remove volatile hydrocarbons.

20. An alkylation process comprising the steps of:
   a. contacting a mixture comprising isoparaffins and n-olefins with an acidic alkylation catalyst system comprising a catalyst system comprising i.) a solid catalyst component of a transition alumina or zeolite which has been previously contacted with a Lewis acid, and ii.) free Lewis acid, under alkylation conditions to produce an alkylate stream,
   b. separating the alkylate stream from the solid alkylation catalyst system,
   c. contacting the solid alkylation catalyst with a solvent comprising $SO_2$,
   d. separating the solid alkylation catalyst component from the $SO_2$ solvent, and
   d. recycling the solid alkylation catalyst component to the alkylation step.

21. The process of claim 20 where the transition alumina is selected from gamma-alumina, eta-alumina, theta-alumina, chi-alumina, kappa-alumina, lambda-alumina, rho-alumina, and mixtures.

22. The process of claim 21 where the transition alumina is gamma-alumina, eta-alumina, or mixtures.

23. The process of claim 20 where the strong Lewis acid is selected from $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$, and $FeBr_3$.

24. The process of claim 23 where the strong Lewis acid is selected from $SbF_5$, $AlCl_3$, and $BF_3$.

25. The process of claim 24 where the strong Lewis acid is $BF_3$.

26. The process of claim 25 where the $BF_3$ is contacted with the solid alkylation catalyst at a pressure above the pressure of the reaction before the catalyst is recycled.

27. The process of claim 30 additionally comprising the step of heating the solid alkylation catalyst component to a temperature of up to about 75° C. after the separation step to substantially remove volatile hydrocarbons.

28. The process of claim 20 where alkylation conditions include a temperature in the range of $-30°$ C. to 50° C.

29. The process of claim 20 where the mixture comprises 2-butene and isoparaffin.

30. The process of claim 20 including the step of mixing the alkylate stream with other hydrocarbons to produce a gasoline blending component or gasoline.

31. A method for regenerating an acidic, solid, hydrocarbon conversion catalyst which has been deactivated through the deposition of a hydrocarbonaceous reaction product residue having a hydrogen to carbon ratio greater than 1, wherein said hydrocarbon conversion catalyst does not contain a significant lewis acid component, the method comprising the steps of:
   a. separating the acidic, solid, hydrocarbon conversion catalyst from a hydrocarbon conversion reaction medium,
   b. contacting the acidic, solid, hydrocarbon conversion catalyst with a $SO_2$ solvent, and
   c. separating the catalyst component from the $SO_2$ solvent.

* * * * *